United States Patent [19]

Cooper

[11] 4,115,383

[45] Sep. 19, 1978

[54] ALKOXYCARBONYL-ETHYLTHIO-AZETIDINONES AND PROCESS FOR THEIR PREPARATION

[75] Inventor: Robin D. G. Cooper, Indianapolis, Ind.

[73] Assignee: Eli Lilly and Company, Indianapolis, Ind.

[21] Appl. No.: 669,938

[22] Filed: Mar. 24, 1976

Related U.S. Application Data

[63] Continuation-in-part of Ser. No. 660,209, Feb. 23, 1976, abandoned.

[51] Int. Cl.$^2$ .................. C07D 705/08; A01N 31/395
[52] U.S. Cl. ........................... 260/239 A; 260/326 S; 424/244; 548/301
[58] Field of Search .............. 260/239 A, 326 S, 309.7

[56] References Cited

U.S. PATENT DOCUMENTS

| 3,872,086 | 3/1975 | Barton et al. ................ 260/239 A |
| 3,900,487 | 8/1975 | Underwood et al. ........... 260/239.1 |
| 3,920,696 | 11/1975 | Kukdja et al. ................. 260/239 A |
| 3,927,013 | 12/1975 | Barton et al. ................. 260/239 A |
| 3,953,424 | 4/1976 | Barton et al. ................. 260/239 A |
| 3,991,069 | 11/1976 | Barton et al. ................. 260/239 A |

FOREIGN PATENT DOCUMENTS

| 960,677 | 1/1975 | Canada. |
| 2,046,823 | 3/1972 | Fed. Rep. of Germany. |
| 1,368,233 | 9/1974 | United Kingdom. |
| 1,368,234 | 9/1974 | United Kingdom. |

OTHER PUBLICATIONS

Ager et al., J.C.S. Chem. Comm., 1972, 601.
Bachi et al., J.C.S., Perkins I, p. 2326 (1972).
Soma et al., Chem. Abs., 82, 156034t (1975).

*Primary Examiner*—Paul M. Coughlan, Jr.
*Assistant Examiner*—Mark L. Berch
*Attorney, Agent, or Firm*—William C. Martens, Jr.; Everet F. Smith

[57] ABSTRACT

2-Sulfinyl (or thio)-α-isopropenyl (or isopropylidene)-3-amido(or imido)-4-oxo-1-azetidineacetic acids and esters are prepared directly or indirectly from the reaction of a penicillin sulfoxide ester with an ester of acrylic acid. These compounds are active antimicrobial agents or are intermediates to active antimicrobial compounds.

4 Claims, No Drawings

ALKOXYCARBONYL-ETHYLTHIO-AZETIDINONES AND PROCESS FOR THEIR PREPARATION

CROSS REFERENCE

This application is a continuation-in-part of U.S. application Ser. No. 660,209 filed Feb. 23, 1976, now abandoned.

BACKGROUND OF THE INVENTION

This invention relates to novel compounds, some of which are useful as intermediates to antibacterially active compounds and others of which are themselves antibacterially active. The compounds of this invention can be classified as particularly substituted azetidin-2-ones and, for purposes herein, will be named as derivatives of 1-azetidineacetic acid.

The compounds of this invention all result ultimately from the reaction of a penicillin sulfoxide with an ester of acrylic acid.

SUMMARY OF THE INVENTION

This invention relates to compounds of the formula

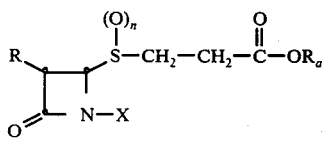

in which X is

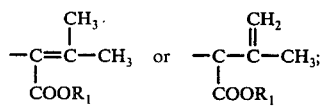

$n$ is 0 or 1; $R_a$ is $C_1$-$C_4$ alkyl;
$R_1$ is hydrogen or a carboxy protecting group; and
R is
 (a) phthalimido;
 (b) an amido group of the formula

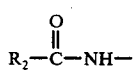

in which $R_2$ is
 (1) hydrogen, $C_1$-$C_3$ alkyl, halomethyl, thienyl-2-methyl, 4-protected-amino-4-protected carboxybutyl, benzyloxy, 4-nitrobenzyloxy, t-butyloxy, 2,2,2-trichloroethoxy, 4-methoxybenzyloxy;
 (2) a group of the formula $R'$-$(O)_m$-$CH_2$- in which $m$ is 0 or 1, and $R'$ is phenyl or phenyl substituted with 1 or 2 halogens, protected hydroxy, nitro, cyano, trifluoromethyl, $C_1$-$C_4$ alkyl, or $C_1$-$C_2$ alkoxy;
 (3) a group of the formula

in which $R'$ is as defined above and W is protected hydroxy, protected carboxy, or protected amino; or
 (c) an imidazolidinyl group of the formula

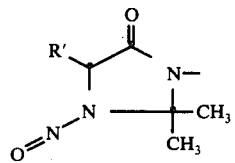

in which $R'$ is as defined above.

Another embodiment of this invention involves a process for preparing a compound of the formula

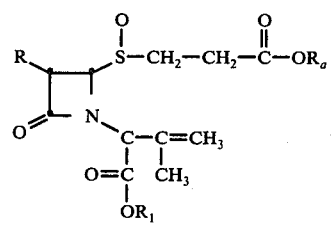

which comprises contacting a penicillin sulfoxide of the formula

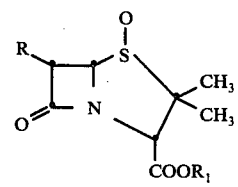

with at least an equimolar amount of an acrylate ester of the formula

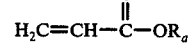

at a temperature of from about 70° C. to about 110° C., wherein, in the above formulae, R, $R_1$ and $R_a$ are as hereinbefore defined.

DETAILED DESCRIPTION OF THE INVENTION

As delineated hereinabove, this invention relates to compounds of the formula

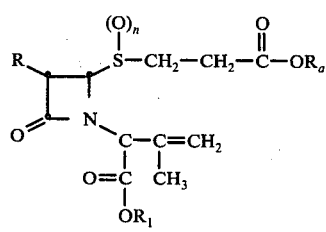

and to compounds of the formula

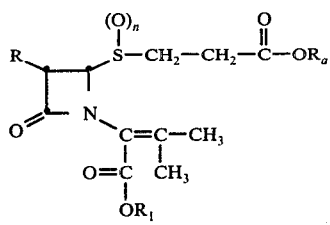

The former of the above structures in which n is 1 is prepared by a process which constitutes another aspect of this invention. These compounds are named as derivatives of 2-sulfinyl-α-isopropenyl-4-oxo-3-amido-(or imido)-1-azetidineacetic acids and are prepared from penicillin sulfoxides by the method to be developed in detail hereinafter. Since these compounds contain an isopropenyl group and thus a double bond defined by a terminal methylene function, they will be referred to herein by the shorthand term "terminal double bond" compounds.

The latter of the two groups of the above compounds is available from the foregoing terminal double bond compounds. When n is 1, these compounds are named as derivatives of 2-sulfinyl-α-isopropylidene-4-oxo-3-amido-(or imido)-1-azetidineacetic acids, and, when n is zero, these compounds are named as derivatives of 2-thio-α-isopropylidene-4-oxo-3-amido-(or imido)-1-acetidineacetic acids. These latter two groups of compounds differ from the former primarily by having an isopropylidene group instead of an isopropenyl group. The isopropylidene compounds have a double bond at a position which is not at the end of the chain, and, therefore, these compounds are referred to herein as the "internal double bond" compounds.

Another aspect of this invention relates to a process for the preparation of the external bond compounds. These compounds are prepared from penicillin sulfoxides of the formula

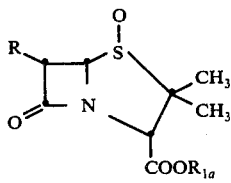

in which R is as hereinbefore defined and $R_{1a}$ is a carboxy protecting group.

The penicillin sulfoxide is reacted with an ester of acrylic acid. The ester reactant has the formula

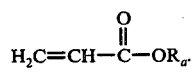

In the foregoing acrylate ester formula, $R_a$ is $C_1$-$C_4$ alkyl, and, preferably, is methyl or ethyl. By "$C_1$-$C_4$ alkyl" is meant any of methyl, ethyl, n-propyl, isopropyl, n-butyl, isobutyl, t-butyl, and sec-butyl.

Typical of these acrylic acid esters are methyl acrylate, ethyl acrylate, n-propyl acrylate, isopropyl acrylate, n-butyl acrylate, isobutyl acrylate, t-butyl acrylate, and sec-butyl acrylate.

$R_1$ in the above formulae denotes hydrogen or a carboxylic acid protecting group. For purposes herein, this latter term can be considered equivalent to the terms "carboxy protecting group" and "protected carboxy". In the event that $R_1$ is a carboxylic acid protecting group, it is preferred that it be one which is removable by acid treatment or by hydrogenation. Preferred such carboxylic acid protecting groups include, for example, $C_1$-$C_3$ alkyl, $C_4$-$C_6$ tert-alkyl, 2,2,2-trichloroethyl, 2-iodoethyl, benzyl, p-nitrobenzyl, succinimidomethyl, phthalimidomethyl, p-methoxybenzyl, benzhydryl, $C_2$-$C_6$ alkanoyloxymethyl, phenacyl, or p-halophenacyl, in which halo denotes chloro, bromo, or iodo.

Specific illustrations of the preferred carboxylic acid protecting groups which are present in the compounds of this invention include, for example, methyl, t-butyl, t-amyl, t-hexyl, 2,2,2-trichloroethyl, 2-iodoethyl, benzyl, p-nitrobenzyl, succinimidomethyl, phthalimidomethyl, p-methoxybenzyl, benzhydryl, acetoxymethyl, pivaloyloxymethyl, propionoxymethyl, phenacyl, p-chlorophenacyl, p-bromophenacyl, and the like.

Highly preferred carboxylic acid protecting groups are t-butyl, benzyl, p-nitrobenzyl, p-methoxybenzyl, benzhydryl, and 2,2,2-trichloroethyl.

R represents the substituents which is present in the 3-position of the azetidinyl moiety of the compounds of this invention. R can be any of three possibilities or classes of possibilities. Of course, the structure of the R group in the compounds of this invention will depend upon the structure of the substituent R which appears in the 6-position of the penicillin sulfoxide starting material employed in the process of this invention and from which the compounds of this invention are prepared. First, R can be an imido function, specifically phthalimido.

Secondly, R can be an amido function of the formula

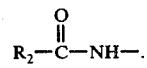

Specific illustrations of the group $R_2$ include, for example, hydrogen, methyl, ethyl, n-propyl, isopropyl, chloromethyl, bromomethyl, thienyl-2-methyl, 4-acetamido-4-p-nitrobenzyloxycarbonylbutyl, benzyloxy, 4-nitrobenzyloxy, t-butyloxy, 2,2,2-trichloroethoxy, 4-methoxybenzyloxy, and the like.

Specific illustrations of the group $R_2$ when it is $R'$-$(O)_m$-$CH_2$ and when m is 0 include, for example, benzyl, 3-bromobenzyl, 2,5-dichlorobenzyl, 4-chloroacetoxybenzyl, 2-nitrobenzyl, 3-cyanobenzyl, 4-trifluoromethylbenzyl, 3-methylbenzyl, 4-n-butylbenzyl, 2-methoxybenzyl, 3-ethoxybenzyl, and the like.

Specific illustrations of the group $R_2$ when it is $R'$-$(O)_m$-$CH_2$- and m is 1 include, for example, phenoxymethyl, 3-iodophenoxymethyl, 4-fluorophenoxymethyl, 3-benzyloxyphenoxymethyl, 4-benzhydryloxyphenoxymethyl, 3-trityloxyphenoxymethyl, 4-nitrobenzyloxyphenoxymethyl, 3-nitrophenoxymethyl, 4-cyanophenoxymethyl, 2-trifluoromethylphenoxymethyl, 3-methylphenoxymethyl, 4-n-propylphenoxymethyl, 4-n-butylphenoxymethyl, 3-methoxyphenoxymethyl, 4-ethoxyphenoxymethyl, and the like.

Specific illustrations of the group $R_2$ when it is

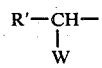

include, for example, α-benzhydryloxybenzyl, α-(4-methoxybenzyloxy)benzyl, α-(2,2,2-trichloroethoxycarbonylamino)benzyl, α-(benzyloxy)-4-bromobenzyl, α-(benzhydryloxycarbonyl)-3-chlorobenzyl, α-(4-nitrobenzyloxycarbonylamino)-4-fluorobenzyl, α,4-di(-formyloxy)benzyl, α-(4-nitrobenzyloxycarbonyl)-3-chloroacetoxybenzyl, α-(4-methoxybenzyloxycarbonylamino)-4-benzhydryloxybenzyl, α-benzyloxy-3-nitrobenzyl, α-(4-nitrobenzyloxycarbonyl)-2-cyanobenzyl, α-(t-butoxycarbonylamino)-4-trifluoromethylbenzyl, α-formyloxy-4-methylbenzyl, α-benzyloxycarbonyl-3-n-butylbenzyl, α-(benzyloxycarbonylamino)-4-methoxybenzyl, α-formyloxy-3-ethoxybenzyl, and the like.

In those instances in which R is

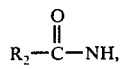

it is preferred that $R_2$ is benzyl or phenoxymethyl, thereby defining phenylacetamido or phenoxyacetamido, respectively.

In portions of the definition provided herein for the group $R_2$, the terms "protected amino", "protected hydroxy", and "protected carboxy" are employed.

The term "protected amino", when employed herein, refers to an amino group substituted with one of the commonly employed amino blocking groups such as t-butyloxycarbonyl (t-BOC), benzyloxycarbonyl, 4-methoxybenzyloxycarbonyl, 4-nitrobenzyloxycarbonyl, 2,2,2-trichloroethoxycarbonyl, diphenylmethoxycarbonyl, isobutyloxycarbonyl, cyclopentyloxycarbonyl, cyclohexyloxycarbonyl, chloroacetyl, dichloroacetyl, 2-chloropropionyl, 3-phenylpropionyl, 4-chlorobutyryl, benzyl, trityl, and the like. Additional typical amino protecting groups are described by J. W. Barton in *Protective Groups in Organic Chemistry*, J. F. W. McOmie, Ed., Plenum Press, New York, N.Y., 1973, Chapter 2. Any of these are recognized as useful within the meaning of the term "protected amino" employed herein.

The term "protected hydroxy", when employed herein, refers to the readily cleavable groups formed with a hydroxyl group such as formyloxy, chloroacetoxy, benzyloxy, benzhydryloxy, trityloxy, 4-nitrobenzyloxy, and the like. Other hydroxy protecting groups, including those described by C. B. Reese in *Protective Groups in Organic Chemistry, supra,* Chapter 3, are considered to be within the term "protected hydroxy" as used herein.

The term "protected carboxy", when employed herein, refers to a carboxy group which has been protected by one of the commonly used carboxylic acid protecting groups employed to block or protect the carboxylic acid functionality of a compound while a reaction or sequence of reactions involving other functional sites of the compound are carried out. Such protected carboxy groups are noted for their ease of cleavage to the corresponding carboxylic acid by hydrolytic or by hydrogenolytic methods. Any of those groups defined hereinabove for $R_1$ are also included within the meaning of the term "protected carboxy". Examples of carboxylic acid protecting groups include methyl, t-butyl, benzyl, 4-methoxybenzyl, $C_2$-$C_6$ alkanoyloxymethyl, 2-iodoethyl, 4-nitrobenzyl, diphenylmethyl (benzhydryl), phenacyl, p-halophenacyl, 2,2,2-trichloroethyl, succinimidomethyl, and like ester forming moieties. The nature of such ester forming groups is not critical; it is preferred, however, that the ester formed therewith be stable under the reaction conditions of the process of this invention. Other known carboxy protecting groups such as those described by E. Haslam in *Protective Groups in Organic Chemistry, supra*, Chapter 5, are considered to be within the term "protected carboxy" as used herein.

Preferred groups within the term "protected carboxy" are tert-butyl, benzyl, p-methoxybenzyl, p-nitrobenzyl, benzhydryl, and 2,2,2-trichloroethyl.

In the foregoing definitions, hydroxy amino, and carboxy protecting groups, of course, are not exhaustively described. The purpose of these groups it to protect reactive functional groups during preparation of a desired product. They then are removed without disruption of the remainder of the molecule. Many such protecting groups are well known in the art, and their use is equally applicable in the process of this invention.

In addition, the group R of the compounds of this invention can be an imidazolidinyl group of the formula

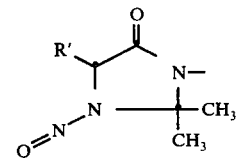

in which R' is phenyl or phenyl substituted with 1 or 2 halogens, protected hydroxy, nitro, cyano, trifluoromethyl, $C_1$-$C_4$ alkyl, or $C_1$-$C_2$ alkoxy.

R' in the above imidazolidinyl formula typically includes phenyl, 3-bromophenyl, 2-chlorophenyl, 4-fluorophenyl, 3-iodophenyl, 3-chloro-4-fluorophenyl, 2-chloro4-bromophenyl, 4-formyloxyphenyl, 3-formyloxyphenyl, 4-nitrophenyl, 2-cyanophenyl, 3-trifluoromethylphenyl, 4-methylphenyl, 3-ethylphenyl, 4-isopropylphenyl, 4-t-butylphenyl, 3-methoxyphenyl, 2-ethoxyphenyl, 4-methoxyphenyl, and the like.

Compounds in which R is the aforedescribed imidazolidinyl group can be prepared in accordance with known techniques by reacting a penicillin compound in which R is

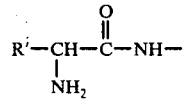

with acetone under moderately basic conditions to produce the corresponding compound in which R is a labile intermediate of the formula

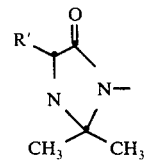

This product then is converted to the stable N-nitroso derivative in which R is the aforedescribed imidazolidinyl group. The latter conversion is accomplished by treatment of the intermediate with sodium nitrite under acidic conditions and with cooling. The resulting penicillin product then is oxidized to its corresponding sulfoxide by routine methods, for example, by treatment with m-chloroperbenzoic acid.

The reaction between the penicillin sulfoxide and the $C_1$–$C_4$ alkyl ester of acrylic acid to prepare the external double bond compound of this invention preferably is carried out at an elevated temperature of from about 70° C. to about 100° C. The reaction is accomplished employing molar equivalents of the penicillin sulfoxide and the acrylate ester. However, generally, a moderate excess, for example, about 10 percent on a molar basis, of the acrylate ester is employed when the reaction is carried out in the presence of an inert solvent. It is possible also to employ the acrylate ester itself as solvent. In such case, a large solvent excess of the acrylate ester is employed, and the penicillin sulfoxide reactant is added thereto. The resulting mixture then is heated to the temperature of reaction and maintained thereat for a time sufficient to accomplish production of the external double bond product.

As noted, an inert organic solvent can be employed in conjunction with the two reactants. Any solvent inert to the reactants and having a boiling point of sufficient elevation to permit the temperature of reaction to be obtained and maintained can be employed. Typical such solvents include, for example, ethers, such as tetrahydrofuran (THF), dioxane, and the like; aromatic hydrocarbons such as benzene, toluene, xylene, and the like; halogenated hydrocarbons, such as methylene bromide, chloroform, bromoform, dichloroethane, chlorobenzene, dichlorobenzene, and the like; esters, such as ethyl acetate, and the like; and various other typical inert solvents.

The reaction mixture, whether in the presence of an inert solvent or not, is brought to the temperature of reaction and maintained thereat for a period sufficient to accomplish producton of the external double bond compound of this invention. Generally, this time of reaction will be from about 3 hours to about 48 hours.

Furthermore, in order to avoid undesirable side reactions, it is preferred that the reaction be carried out in the presence of an inert atmosphere, such as would be obtained by the continuous maintenance of the reaction system in a nitrogen environment.

Upon completion of the reaction, the product can be isolated by means of any of several generally recognized procedures. Typically, the product will be isolated merely by evaporation of any excess acrylate ester as well as the solvent, if any of the latter is present. The resulting product residue can be further purified, if desired, by any of a number of commonly used purificaton techniques, including column chromatography, gas chromatography, crystallization, and related methods.

As indicated hereinabove, the product which results from this reaction has the following formula:

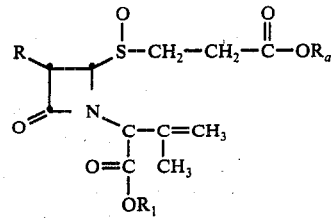

The above product is useful as an intermediate in the preparation of either of two antibiotically active products. First, the intermediate can be cyclized to produce the corresponding $\Delta^3$-desacetoxycephalosporin ester. Ring closure of the external double bond compound to the cephalosporin ester is accomplished employing conditions such as those employed in the traditional penicillin sulfoxide ring expansion process. This process is taught in U.S. Pat. No. 3,275,626. Ring closure to the $\Delta^3$-desacetoxycephalosporin ester is effected by treating the external double bond compound of this invention under acidic conditions. Examples of suitable acids which can be employed to achieve ring closure to the $\Delta^3$-desacetoxycephalosporin ester include sulfuric acid, phosphoric acid, and other mineral acids; sulfonic acids, such as p-toluenesulfonic acid, benzenesulfonic acid, naphthalenesulfonic acid, and the like; Lewis acids, such as boron trifluoride, aluminum chloride, and the like; acid anhydrides such as acetic anhydride, propionic anhydride, benzoic anhydride, and the like.

The resulting $\Delta^3$-desacetoxycephalosporin ester is converted to an antibiotically active cephalosporin compound by cleavage of the ester function in the 4-position to produce the corresponding $\Delta^3$-desacetoxycephalosporin acid. This cleavage is accomplished employing recognized techniques. Deesterification can be achieved, depending upon the nature of the protecting group, by any of several recognized procedures, including (1) treatment with an acid such as trifluoroacetic acid, formic acid, hydrochloric acid, or the like; (2) treatment with zinc and an acid such as formic acid, acetic acid, or hydrochloric acid, or (3) hydrogenation in the presence of palladium, platinum, rhodium, or a compound thereof, in suspension, or on a carrier such as barium sulfate, carbon, alumina, or the like. The literature well recognizes that the free acid cephalosporin which is obtained exhibits potent antibiotic activity.

Secondly, the external double bond compound of this invention can be converted to its corresponding internal double bond compound, also a compound of this invention, by treatment of the former with a mild organic base, such as a tertiary amine, for example, triethylamine, pyridine, or the like. The compound which thereby is produced is termed herein as the internal double bond compound due to the position of the double bond in the isopropyl moiety of the molecule. The internal double bond compound is useful as an intermediate to antibiotically active compounds by the following sequence:

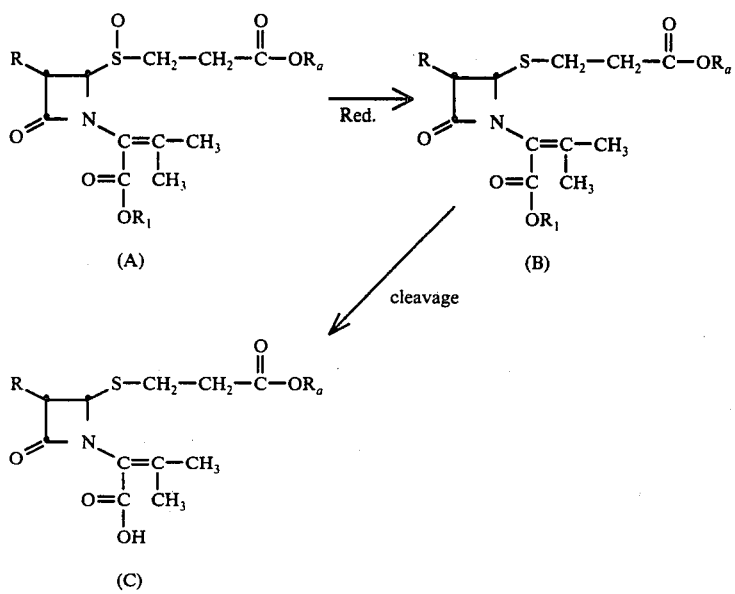

(A) → Red. → (B)

(B) → cleavage → (C)

The first reaction in this sequence comprises a reduction of the sulfoxide moiety to a sulfide. This can be accomplished by reacting the sulfoxide compound with at least one equivalent of phosphorous tribromide in an inert solvent. The reaction generally is carried out at a temperature of from about −20° C. to about +30° C. for a period of from about 5 minutes to about 12 hours. The resulting product, also a compound of this invention is designated a 2-[(2-substituted carboxyethyl)thio]-α-isopropenyl-4-oxo-3-imido-(or amido)-1-azetidineacetic acid ester. This latter compound also participates in the broad definition of the class of compounds described herein as inernal double bond compounds. The thio compound can be converted to an antibiotically active compound by cleavage of the ester function of the azetidineacetic acid moiety. Cleavage can be carried out under conditions described hereinabove with respect to the Δ$^3$-desacetoxycephalosporin ester cleavage. The resulting product has the structure of the foregoing Formula C. Compounds of this class exhibit useful antimicrobial activity.

It will be recognized that the reaction sequences described hereinabove can be varied such that the ultimate products are derived through a different set of intermediates. Thus, the external double bond compound which results from the reaction of the penicillin sulfoxide with the acrylate ester can be cleaved to a compound in which R$_1$ is hydrogen, also a compound of this invention. This cleavage is accomplished in accordance with the methods described hereinabove. The resulting free acid external bond compound then can be converted by ring closure to the free acid Δ$^3$-desacetoxycephalosporin.

Correspondingly, the free acid external double bond compound can be isomerized as hereinbefore described to the corresponding internal double bond compound. The resulting free acid internal double bond compound also constitutes a compound of this invention. This latter compound then can be reduced to the corresponding thio compound, an antimicrobially active compound of this invention.

Furthermore, the external double bond compound of this invention can be reduced in the aforedescribed manner to the corresponding thio compound which then can be converted as described above to the internal double bond thio compound of this invention.

Examples of the compounds of this invention include the followng:

t-butyl 2-[(2-methoxycarbonyl)ethylsulfinyl]-α-isopropenyl-4-oxo-3-formamido-1-azetidineacetate;

benzyl 2-[(2-methoxycarbonyl)ethylsulfinyl]-α-isopropenyl-4-oxo-3-formamido- b 1-azetidineacetate;

2,2,2-trichloroethyl 2-[(2-ethoxycarbonyl)ethylsulfinyl]-α-isopropenyl-4-oxo-3-acetamido-1-azetidineacetate;

p-nitrobenzyl 2-[(2-ethoxycarbonyl)ethylsulfinyl]-α-isopropenyl-4-oxo-3-butyramido-1-azetidineacetate;

p-methoxybenzyl2-[(2-methoxycarbonyl)ethylsulfinyl]-α-isopropenyl-4-oxo-3-chloroacetamido-1-azetidineacetate;

benzhydryl 2-[(2-ethoxycarbonyl)ethylsulfinyl]-α-isopropenyl-4-oxo-3-(4'-chloroacetamido-4'-benzhydryloxycarbonylvaleramido)-1-azetidineacetate;

p-nitrobenzyl 2[(2-ethoxycarbonyl)ethylsulfinyl]-α-isopropenyl-4-oxo-3-(4'-nitrobenzyloxycarbamido)-1-azetidineacetate;

t-amyl 2l-[(2-n-propoxycarbonyl)ethylsulfinyl]-α-isopropenyl-4-oxo-3-benzyloxycarbamido-1-azetidineacetate;

t-butyl 2-[(2-methoxycarbonyl)ethylsulfinyl]-α-isopropenyl-4-oxo-3-t-butyloxycarbamido-1-azetidineacetate;

2-iodoethyl 2-[(2-ethoxycarbonyl)ethylsulfinyl]-α-isopropenyl-4-oxo-3-(2',2',2'-trichloroethoxycarbamido)-1-azetidineacetate;

acetoxymethyl 2-[(2-isopropoxycarbonyl)ethylsufinyl]-α-isopropenyl-4-oxo-3-(4'-methoxybenzyloxycarbamido)-1-azetidineacetate;

p-methoxybenzyl 2-[(2-ethoxycarbonyl)ethylsulfinyl]-α-isopropenyl-4-oxo-3-phenylacetamido-1-azetidine-acetate;

2,2,2-trichloroethyl 2-[(2-methoxycarbonyl)ethylsulfinyl]-α-isopropenyl-4-oxo-3-phenoxyacetamido-1-acetidineacetate;

p-nitrobenzyl 2-[(2-ethoxycarbonyl)ethylsulfinyl]-α-isopropenyl-4-oxo-3-(2',5'-dichlorophenylacetamido)-1-azetidineacetate;

benzyl 2[(2-methoxycarbonyl)ethylsulfinyl]-α-isopropenyl-4-oxo-3-(3'-bromophenoxyacetamido)-1-azetidineacetate;

t-butyl 2-[(2-ethoxycarbonyl)ethylsulfinyl]-α-isopropenyl-4-oxo-3-(4'-chloroacetoxyphenylacetamido)-1-azetidineacetate;

t-hexyl 2-[(2-n-butoxycarbonyl)ethylsulfinyl]-α-isopropenyl-4-oxo-3-(3'-formyloxyphenoxyacetamido)-1-azetidineacetate;

p-nitrobenzyl 2-[(2-ethoxycarbonyl)ethylsulfinyl]-α-isopropenyl-4-oxo-3-(2'-nitrophenylacetamido)-1-azetidineacetate;

p-methoxybenzyl 2-[(2-methoxycarbonyl)ethylsulfinyl]-α-isopropenyl-4-oxo-3-(4'-nitrophenoxyacetamido)-1-azetidineacetate;

benzhydryl 2-[(2-ethoxycarbonyl)ethylsulfinyl]-α-isopropenyl-4-oxo-3-(3'-cyanophenylacetamido)-1-azetidineacetate;

p-bromophenyl 2-[(2-methoxycarbonyl)ethylsulfinyl]-α-isopropenyl-4-oxo-3-(2'-cyanophenoxyacetamido)-1-azetidineacetate;

propionoxymethyl 2-[(2-t-butoxycarbonyl)ethylsulfinyl]-α-isopropenyl-4-oxo-3-(4'-trifluoromethylphenyl-acetamido)-1-acetidineacetate;

p-nitrobenzyl 2-[(2-ethoxycarbonyl)ethylsulfinyl]-α-isopropenyl-4-oxo-3-(3'-trifluoromethylphenoxyacetamido)-1-azetidineacetate;

t-butyl 2-[(2-ethoxycarbonyl)ethylsulfinyl]-α-isopropenyl-4-oxo-3-(2'-ethylphenylacetamido)-1-azetidineacetate;

acetoxymethyl 2-[(2-ethoxycarbonyl)ethylsulfinyl]-α-isopropenyl-4-oxo-3-(4'-isopropylphenoxyacetamido)-1-azetidineacetate;

t-butyl 2-[(2-methoxycarbonyl)ethylsulfinyl]-α-isopropenyl-4-oxo-3-(3'-ethoxyphenylacetamido)-1-azetidineacetate;

p-nitrobenzyl 2-[(2-methoxycarbonyl)ethylsulfinyl]-α-isopropenyl-4-oxo-3-(4'-methoxyphenoxyacetamido)-1-azetidineacetate;

p-nitrobenzyl 2-[(2-sec-butoxycarbonyl)ethylsulfinyl]-α-isopropenyl-4-oxo-3-(α-formyloxyphenylacetamido)-1-azetidineacetate;

p-methoxybenzyl 2-[(2-methoxycarbonyl)ethylsulfinyl]-α-isopropenyl-4-oxo-3-(α-benzhydryloxyphenylacetamido)-1-azetidineacetate;

benzhydryl 2-[(2-isobutoxycarbonyl)ethylsulfinyl]-α-isopropenyl-4-oxo-3-(α-benzhydryloxycarbonylphenylacetamido)-1-azetidineacetate;

p-nitrobenzyl 2-[(2-methoxycarbonyl)ethylsulfinyl]-α-isopropenyl-4-oxo-3-(α-benzyloxycarbonylaminophenylacetamido)-1-azetidineacetate;

t-butyl 2-[(2-ethoxycarbonyl)ethylsulfinyl]-α-isopropenyl-4-oxo-3-(α-t-butyloxycarbonylaminophenylacetamido)-1-azetidineacetate;

p-nitrobenzyl 2-[(2-methoxycarbonyl)ethylsulfinyl]-α-isopropenyl-4-oxo-3-(2'-thienylacetamido)-1-acetidineacetate;

t-amyl 2-[(2-ethoxycarbonyl)ethylsulfinyl]-α-isopropylidene-4-oxo-3-benzyloxycarbamido-1-azetidineacetate;

t-butyl 2-[(2-ethoxycarbonyl)ethylsulfinyl]-α-isopropylidene-4-oxo-3-t-butyloxycarbamido-1-azetidineacetate;

t-hexyl 2-[(2-sec-butoxycarbonyl)ethylsulfinyl]-α-isopropylidene-4-oxo-3-(3'-formyloxyphenoxyacetamido)-1-azetidineacetate;

p-nitrobenzyl 2-[(2-ethoxycarbonyl)ethylsulfinyl]-α-isopropylidene-4-oxo-3-(2'-nitrophenylacetamido)-1-azetidineacetate;

p-methoxybenzyl 2-[(2-isobutoxycarbonyl)ethylsulfinyl]-α-isopropylidene-4-oxo-3-(4'-nitrophenoxyacetamido)-1-acetidineacetate;

benzhydryl 2-[(2-methoxycarbonyl)ethylsulfinyl]-α-isopropylidene-4-oxo-3-(3'-cyanophenylacetamido)-1-azetidineacetate;

p-bromophenacyl 2-[(2-ethoxycarbonyl)ethylsulfinyl]-α-isopropylidene-4-oxo-3-(2'-cyanophenoxyacetamido)-1-azetidineacetate;

propionoxymethyl 2-[(2-methoxycarbonyl)ethylsulfinyl]-α-isopropylidene-4-oxo-3-(4'-trifluoromethylphenylacetamido)-1-azetidineacetate;

p-nitrobenzyl 2-[(2-ethoxycarbonyl)ethylsulfinyl]-α-isopropylidene-4-oxo-3-(3'-trifluoromethylphenoxyacetamido)-1-azetidineacetate;

t-butyl 2-[(2-ethoxycarbonyl)ethylsulfinyl]-α-isopropylidene-4-oxo-3-(2'-ethylphenylacetamido)-1-azetidineacetate;

acetoxymethyl 2-[(2-methoxycarbonyl)ethylsulfinyl]-α-isopropylidene-4-oxo-3-(4'-isopropylphenoxyacetamido)-1-azetidineacetate;

t-butyl 2-[(2-methoxycarbonyl)ethylsulfinyl]-α-isopropylidene-4-oxo-3-(3'-ethoxyphenylacetamido)-1-azetidineacetate; p-nitrobenzyl 2-[(2-methoxycarbonyl)ethylsulfinyl]-α-isopropylidene-4-oxo-3-(4'-methoxyphenoxyacetamido)-1-azetidineacetate;

p-nitrobenzyl 2-[(2-methoxycarbonyl)ethylsulfinyl]-α-isopropylidene-4-oxo-3-(α-formyloxyphenylacetamido)-1-azetidineacetate;

p-methoxybenzyl 2-[(2-ethoxycarbonyl)ethylsulfinyl]-α-isopropylidene-4-oxo-3-(α-benzhydryloxyphenylacetamido)-1-azetidineacetate;

benzhydryl 2-[(2-ethoxycarbonyl)ethylsulfinyl]-α-isopropylidene-4-oxo-3-(α-benzhydryloxycarbonylphenylacetamido)1-azetidineacetate;

p-nitrobenzyl 2-[(2-methoxycarbonyl)ethylsulfinyl]-α-isopropylidene-4-oxo-3-(α-benzyloxycarbonylaminophenylacetamido)-1-azetidineacetate;

t-butyl 2-[(2-ethoxycarbonyl)ethylsulfinyl]-α-isopropylidene-4-oxo-3-(α-t-butyloxycarbonylaminophenylacetamido)-1-azetidineacetate;

p-nitrobenzyl 2-[(2-ethoxycarbonyl)ethylsulfinyl]-α-isopropylidene-4-oxo-3-(2'-thienylacetamido)-1-azetidineacetate;

t-butyl 2-[(2-methoxycarbonyl)ethylthio]-α-isopropylidene-4-oxo-3-phthalimido-1-azetidineacetate;

benzyl 2-[(2-methoxycarbonyl)ethylthio]-α-isopropylidene-4-oxo-3-formamido-1-azetidineacetate;

2,2,2-trichloroethyl 2-[(2-n-propoxycarbonyl)-ethylthio]-α-isopropylidene-4-oxo-3-acetamido-1-azetidineacetate;

p-nitrobenzyl 2-[(2-isopropoxycarbonyl)ethylthio]-α-isopropylidene-4-oxo-3-butyramido-1-azetidineacetate;

p-methoxybenzyl 2-[(2-methoxycarbonyl)ethylthio]-α-isopropylidene-4-oxo-3-chloroacetamido-1-azetidineacetate;

benzhydryl 2-[(2-methoxycarbonyl)ethylthio]-α-isopropylidene-4-oxo-3-(4'-chloroacetamido-4'-benzhydryloxycarbonylvaleramido)-1-azetidineacetate;

p-nitrobenzyl 2-[(2-methoxycarbonyl)ethylthio]-α-isopropylidene-4-oxo-3-(4'-nitrobenzyloxycarbamido)-1-azetidineacetate;

t-amyl 2-[(2-n-butoxycarbonyl)ethylthio]-α-isopropylidene-4-oxo-3-benzyloxycarbamido-1-azetidineacetate;

t-butyl 2-[(2-isobutoxycarbonyl)ethylthio]-α-isopropylidene-4-oxo-3-t-butyloxycarbamido-1-azetidineacetate;

2-iodoethyl 2-[(2-ethoxycarbonyl)ethylthio]-α-isopropylidene-4-oxo-3-(2',2',2'-trichloroethoxycarbamido)-1-azetidineacetate;

acetoxymethyl 2-[(2-methoxycarbonyl)ethylthio]-α-isopropylidene-4-oxo-3-(4'-methoxybenzyloxycarbamido)-1-azetidineacetate;

p-methoxybenzyl 2-[(2-t-butoxycarbonyl)ethylthio]-α-isopropylidene-4-oxo-3-phenylacetamido-1-azetidineacetate;

2,2,2-trichloroethyl 2-[(2-sec-butoxycarbonyl)-ethylthio]-α-isopropylidene-4-oxo-3-phenoxyacetamido-1-azetidineacetate;

p-nitrobenzyl 2-[(2-ethoxycarbonyl)ethylthio]-α-isopropylidene-4-oxo-3-(2',5'-dichlorophenylacetamido)-1-azetidineacetate;

benzyl 2-[(2-methoxycarbonyl)ethylthio]-α-isopropylidene-4-oxo-3-(3'-bromophenoxyacetamido)-1-azetidineacetate;

t-butyl 2-[(2-ethoxycarbonyl)ethylthio]-α-isopropylidene-4-oxo-3-(4'-chloroacetoxyphenylacetamido)-1-azetidineacetate;

t-hexyl 2-[(2-isobutoxycarbonyl)ethylthio]-α-isopropylidene-4-oxo-3-(3'-formyloxyphenoxyacetamido)-1-azetidineacetate;

p-nitrobenzyl 2-[(2-ethoxycarbonyl)ethylthio]-α-isopropylidene-4-oxo-3-(2'-nitrophenylacetamido)-1-azetidineacetate;

p-methoxyphenyl 2-[(2-isopropoxycarbonyl)ethylthio]-α-isopropylidene-4-oxo-3-(4'-nitrophenoxyacetamido)-1-azetidineacetate;

benzhydryl 2-[(2-methoxycarbonyl)ethylthio]-α-isopropylidene-4-oxo-3-(3'-cyanophenylacetamido)-1-azetidineacetate;

p-bromophenacyl 2-[(2-ethoxycarbonyl)ethylthio]-α-isopropylidene-4-oxo-3-(2'-cyanophenoxyacetamido)-1-azetidineacetate;

propionoxymethyl 2-[(2-n-propoxycarbonyl)ethylthio]-α-isopropylidene-4-oxo-3-(4'-trifluoromethylphenylacetamido)-1-azetidineacetate;

p-nitrobenzyl 2-[(2-ethoxycarbonyl)ethylthio]-α-isopropylidene-4-oxo-3-(3'-trifluoromethylphenoxyacetamido)-1-azetidineacetate;

t-butyl 2-[(2-ethoxycarbonyl)ethylthio]-α-isopropylidene-4-oxo-3-(2'-ethylphenylacetamido)-1-azetidineacetate;

acetoxy 2-[(2-n-butoxycarbonyl)ethylthio]-α-isopropylidene-4-oxo-3-(4'-isopropylphenoxyacetamido)-1-azetidineacetate;

t-butyl 2-[(2-methoxycarbonyl)ethylthio]-α-isopropylidene-4-oxo-3-(3'-ethoxyphenylacetamido)-1-azetidineacetate;

p-nitrobenzyl 2-[(2-methoxycarbonyl)ethylthio]-α-isopropylidene-4-oxo-3-(4'-methoxyphenoxyacetamido)-1-azetidineacetate;

p-nitrobenzyl 2-[(2-methoxycarbonyl)ethylthio]-α-isopropylidene-4-oxo-3-(α-formyloxyphenylacetamido)-1-azetidineacetate;

p-methoxybenzyl 2-[(2-ethoxycarbonyl)ethylthio]-α-isopropylidene-4-oxo-3-(α-benzhydryloxyphenylacetamido)-1-azetidineacetate;

benzhydryl 2-[(2-n-butoxycarbonyl)ethylthio]-α-isopropylidene-4-oxo-3-(α-benzhydryloxycarbonylphenylacetamido)-1-azetidineacetate;

p-nitrobenzyl 2-[(2-methoxycarbonyl)ethylthio]-α-isopropylidene-4-oxo-3-(α-benzyloxycarbonylaminophenylacetamido)-1-azetidineacetate;

t-butyl 2-[(2-ethoxycarbonyl)ethylthio]-α-isopropylidene-4-oxo-3-(α-t-butyloxycarbonylaminophenylacetamido)-1-azetidineacetate;

p-nitrobenzyl 2-[(2-ethoxycarbonyl)ethylthio]-α-isopropylidene-4-oxo-3-(2'-thienylacetamido)-1-azetidineacetate;

2-[(2-methoxycarbonyl)ethylthio]-α-isopropylidene-4-oxo-3-phthalimido-1-azetidineacetic acid;

2-[(2-methoxycarbonyl)ethylthio]-α-isopropylidene-4-oxo-3-formamido-1-azetidineacetic acid;

2-[(2-n-propoxycarbonyl)ethylthio]-α-isopropylidene-4-oxo-3-acetamido-1-azetidineacetic acid;

2-[(2-isopropoxycarbonyl)ethylthio]-α-isopropylidene-4-oxo-3-butyramido-1-azetidineacetic acid;

2-[(2-methoxycarbonyl)ethylthio]-α-isopropylidene-4-oxo-3-chloroacetamido-1-azetidineacetic acid;

2-[(2-n-butoxycarbonyl)ethylthio]-α-isopropylidene-4-oxo-3-(4'-chloroacetamido-4'-benzhydryloxycarbonylvaleramido)-1-azetidineacetic acid;

2-[(2-methoxycarbonyl)ethylthio]-α-isopropylidene-4-oxo-3-(4'-nitrobenzyloxycarbamido)-1-azetidineacetic acid;

2-[(2-ethoxycarbonyl)ethylthio]-α-isopropylidene-4-oxo-3-benzyloxycarbamido-1-azetidineacetic acid;

2-[(2-t-butoxycarbonyl)ethylthio]-α-isopropylidene-4-oxo-3-t-butyloxycarbamido-1-azetidineacetic acid;

2-[(2-ethoxycarbonyl)ethylthio]-α-isopropylidene-4-oxo-3-(2',2',2'-trichloroethoxycarbamido)-1-azetidineacetic acid;

2-[(2-methoxycarbonyl)ethylthio]-α-isopropylidene-4-oxo-3-(4'-methoxybenzyloxycarbamido)-1-azetidineacetic acid;

2-[(2-sec-butoxycarbonyl)ethylthio]-α-isopropylidene-4-oxo-3-phenylacetamido-1-azetidineacetic acid;

2-[(2-n-butoxycarbonyl)ethylthio]-α-isopropylidene-4-oxo-3-phenoxyacetamido-1-azetidineacetic acid;

2-[(2-ethoxycarbonyl)ethylthio]-α-isopropylidene-4-oxo-3-(2',5'-dichlorophenylacetamido)-1-azetidineacetic acid;

2-[(2-n-propoxycarbonyl)ethylthio]-α-isopropylidene-4-oxo-3-(3'-bromophenoxyacetamido)-1-azetidineacetic acid;

2-[(2-ethoxycarbonyl)ethylthio]-α-isopropylidene-4-oxo-3-(4'-chloroacetoxyphenylacetamido)-1-azetidineacetic acid;

2-[(2-isopropoxycarbonyl)ethylthio]-α-isopropylidene-4-oxo-3-(3'-formyloxyphenoxyacetamido)-1-azetidineacetic acid;

2-[(2-ethoxycarbonyl)ethylthio]-α-isopropylidene-4-oxo-3-(2'-nitrophenylacetamido)-1-azetidineacetic acid;

2-[(2-isobutoxycarbonyl)ethylthio]-α-isopropylidene-4-oxo-3-(4'-nitrophenoxyacetamido)-1-azetidineacetic acid;

2-[(2-methoxycarbonyl)ethylthio]-α-isopropylidene-4-oxo-3-(3'-cyanophenylacetamido)-1-azetidineacetic acid;

2-[(2-ethoxycarbonyl)ethylthio]-α-isopropylidene-4-oxo-3-(2'-cyanophenoxyacetamido)-1-azetidineacetic acid;

2-[(2-methoxycarbonyl)ethylthio]-α-isopropylidene-4-oxo-3-(4'-trifluoromethylphenylacetamido)-1-azetidineacetic acid;

2-[(2-ethoxycarbonyl)ethylthio]-α-isopropylidene-4-oxo-3-(3'-trifluoromethylphenoxyacetamido)-1-azetidineacetic acid;

2-[(2-ethoxycarbonyl)ethylthio]-α-isopropylidene-4-oxo-3-(2'-ethylphenylacetamido)-1-azetidineacetic acid;

2-[(2-methoxycarbonyl)ethylthio]-α-isopropylidene-4-oxo-3-(4'-isopropylphenoxyacetamido)-1-azetidineacetic acid;

2-[(2-methoxycarbonyl)ethylthio]-α-isopropylidene-4-oxo-3-(3'-ethoxyphenylacetamido)-1-azetidineacetic acid;

2-[(2-methoxycarbonyl)ethylthio]-α-isopropylidene-4-oxo-3-(4'-methoxyphenoxyacetamido)-1-azetidineacetic acid;

2-[(2-n-propoxycarbonyl)ethylthio]-α-isopropylidene-4-oxo-3-(α-formyloxyphenylacetamido)-1-azetidineacetic acid;

2-[(2-ethoxycarbonyl)ethylthio]-α-isopropylidene-4-oxo-3-(α-benzhydryloxyphenylacetamido)-1-azetidineacetic acid;

2-[(2-isopropoxycarbonyl)ethylthio]-α-isopropylidene-4-oxo-3-(α-benzyhydryloxycarbonylphenylacetamido)-1-azetidineacetic acid;

2-[(2-methoxycarbonyl)ethylthio]-α-isopropylidene-4-oxo-3-(α-benzyloxycarbonylaminophenylacetamido)-1-azetidineacetic acid;

2-[(2-ethoxycarbonyl)ethylthio]-α-isopropylidene-4-oxo-3-(α-t-butyloxycarbonylaminophenylacetamido)-1-azetidineacetic acid;

2-[(2-ethoxycarbonyl)ethylthio]-α-isopropylidene-4-oxo-3-(2'-thienylacetamido)-1-azetidineacetic acid;

2-[(2-methoxycarbonyl)ethylsulfinyl]-α-isopropenyl-4-oxo-3-phthalimido-1-azetidineacetic acid;

2-[(2-methoxycarbonyl)ethylsulfinyl]-α-isopropenyl-4-oxo-3-formamido-1-azetidineacetic acid;

2-[(2-isopropoxycarbonyl)ethylsulfinyl]-α-isopropenyl-4-oxo-3-acetamido-1-azetidineacetic acid;

2-[(2-n-butoxycarbonyl)ethylsulfinyl]-α-isopropenyl-4-oxo-3-butyramido-1-azetidineacetic acid;

2-[(2-methoxycarbonyl)ethylsulfinyl]-α-isopropenyl-4-oxo-3-chloroacetamido-1-azetidineacetic acid;

2-[(2-n-propoxycarbonyl)ethylsulfinyl]-α-isopropenyl-4-oxo-3-(4'-chloroacetamido-4'-benzhydryloxycarbonylvaleramido)-1-azetidineacetic acid;

2-[(2-ethoxycarbonyl)ethylsulfinyl]-α-isopropenyl-4-oxo-3-(4'-nitrobenzyloxycarbamido)-1-azetidineacetic acid;

2-[(2-isobutoxycarbonyl)ethylsulfinyl]-α-isopropenyl-4-oxo-3-benzyloxycarbamido-1-azetidineacetic acid;

2-[(2-sec-butoxycarbonyl)ethylsulfinyl]-α-isopropenyl-4-oxo-3-t-butyloxycarbamido-1-azetidineacetic acid;

2-[(2-ethoxycarbonyl)ethylsulfinyl]-α-isopropenyl-4-oxo-3-(2',2',2'-trichloroethoxycarbamido)-1-azetidineacetic acid;

2-[(2-t-butoxycarbonyl)ethylsulfinyl]-α-isopropenyl-4-oxo-3-(4'-methoxybenzyloxycarbamido)-1-azetidineacetic acid;

2-[(2-isopropoxycarbonyl)ethylsulfinyl]-α-isopropenyl-4-oxo-3-phenylacetamido-1-azetidineacetic acid;

2-[(2-methoxycarbonyl)ethylsulfinyl]-α-isopropenyl-4-oxo-3-phenoxyacetamido-1-azetidineacetic acid;

2-[(2-ethoxycarbonyl)ethylsulfinyl]-α-isopropenyl-4-oxo-3-(2',5'-dichlorophenylacetamido)-1-azetidineacetic acid;

2-[(2-t-butoxycarbonyl)ethylsulfinyl]-α-isopropenyl-4-oxo-3-(3'-bromophenylacetamido)-1-azetidineacetic acid;

2-[(2-ethoxycarbonyl)ethylsulfinyl]-α-isopropenyl-4-oxo-3-(4'-chloroacetoxyphenylacetamido)-1-azetidineacetic acid;

2-[(2-n-propoxycarbonyl)ethylsulfinyl]-α-isopropenyl-4-oxo-3-(3'-formyloxyphenoxyacetamido)-1-azetidineacetic acid;

2-[(2-ethoxycarbonyl)ethylsulfinyl]-α-isopropenyl-4-oxo-3-(2'-nitrophenylacetamido)-1-azetidineacetic acid;

2-[(2-isobutoxycarbonyl)ethylsulfinyl]-α-isopropenyl-4-oxo-3-(4'-nitrophenoxyacetamido)-1-azetidineacetic acid;

2-[(2-ethoxycarbonyl)ethylsulfinyl]-α-isopropenyl-4-oxo-3-(3'-cyanophenylacetamido)-1-azetidineacetic acid;

2-[(2-methoxycarbonyl)ethylsulfinyl]-α-isopropenyl-4-oxo-3-(2'-cyanophenoxyacetamido)-1-azetidineacetic acid;

2-[(2-methoxycarbonyl)ethylsulfinyl]-α-isopropenyl-4-oxo-3-(4'-trifluoromethylphenylacetamido)-1-azetidineacetic acid;

2-[(2-ethoxycarbonyl)ethylsulfinyl]-α-isopropenyl-4-oxo-3-(2'-ethylphenylacetamido)-1-azetidineacetic acid;

2-[(2-n-propoxycarbonyl)ethylsulfinyl]-α-isopropenyl-4-oxo-3-(4'-isopropylphenoxyacetamido)-1-azetidineacetic acid;

2-[(2-methoxycarbonyl)ethylsulfinyl]-α-isopropenyl-4-oxo-3-(3'-ethoxyphenylacetamido)-1-azetidineacetic acid;

2-[(2-methoxycarbonyl)ethylsulfinyl]-α-isopropenyl-4-oxo-3-(4'-methoxyphenoxyacetamido)-1-azetidineacetic acid;

2-[(2-sec-butoxycarbonyl)ethylsulfinyl]-α-isopropenyl-4-oxo-3-(α-formyloxyphenylacetamido)-1-azetidineacetic acid;

2-[(2-methoxycarbonyl)ethylsulfinyl]-α-isopropenyl-4-oxo-3-(α-benzhydryloxyphenylacetamido)-1-azetidineacetic acid;

2-[(2-isopropoxycarbonyl)ethylsulfinyl]-α-isopropenyl-4-oxo-3-(α-benzhydryloxycarbonylphenylacetamido)-1-azetidineacetic acid;

2-[(2-methoxycarbonyl)ethylsulfinyl]-α-isopropenyl-4-oxo-3-(α-benzyloxycarbonylaminophenylacetamido)-1-azetidineacetic acid;

2-[(2-ethoxycarbonyl)ethylsulfinyl]-α-isopropenyl-4-oxo-3-(α-t-butyloxycarbonylaminophenylacetamido)-1-azetidineacetic acid;

2-[(2-methoxycarbonyl)ethylsulfinyl]-α-isopropenyl-4-oxo-3-(2'-thienylacetamido)-1-azetidineacetic acid;

t-butyl 2-[(2-methoxycarbonyl)ethylthio]-α-isopropenyl-4-oxo-3-phthalimido-1-azetidineacetate;

benzyl 2-[(2-methoxycarbonyl)ethylthio]-α-isopropenyl-4-oxo-3-formamido-1-azetidineacetate;

2,2,2-trichloroethyl 2-[(2-n-butoxycarbonyl)ethylthio]-α-isopropenyl-4-oxo-3-acetamido-1-azetidineacetate;
p-nitrobenzyl 2-[(2-isopropoxycarbonyl)ethylthio]-α-isopropenyl-4-oxo-3-butyramido-1-azetidineacetate;
p-methoxybenzyl 2-[(2-methoxycarbonyl)ethylthio]-α-isopropenyl-4-oxo-3-chloroacetamido-1-azetidineacetate;
benzhydryl 2-[(2-t-butoxycarbonyl)ethylthio]-α-isopropenyl-4-oxo-3-(4'-chloroacetamido-4'-benzhydryloxycarbonylvaleramido)-1-azetidineacetate;
p-nitrobenzyl 2-[(2-methoxycarbonyl)ethylthio]-α-isopropenyl-4-oxo-3-(4'-nitrobenzyloxycarbamido)-1-azetidineacetate;
t-amyl 2-[(2-ethoxycarbonyl)ethylthio]-α-isopropenyl-4-oxo-3-benzyloxycarbamido-1-azetidineacetate;
i-butyl 2-[(2-n-propoxycarbonyl)ethylthio]-α-isopropenyl-4-oxo-3-t-butyloxycarbamido-1-azetidineacetate;
2-iodoethyl 2-[(2-ethoxycarbonyl)ethylthio]-α-ispropenyl-4-oxo-3-(2',2',2'-trichloroethoxycarbamido)-1-azetidineacetate;
acetoxymethyl 2-[(2-t-butoxycarbonyl)ethylthio]-α-isopropenyl-4-oxo-3-(4'-methoxybenzyloxycarbamido)-1-azetidineacetate;
p-methoxybenzyl 2-[(2-n-butoxycarbonyl)ethylthio]-α-isopropenyl-4-oxo-3-phenylacetamido-1-azetidineacetate;
2,2,2-trichloroethyl 2-[(2-n-propoxycarbonyl)ethylthio]-α-isopropenyl-4-oxo-3-phenoxyacetamido-1-azetidineacetate;
p-nitrobenzyl 2-[(2-ethoxycarbonyl)ethylthio]-α-isopropenyl-4-oxo-3-(2',5'-dichlorophenylacetamido)-1-azetidineacetate;
benzyl 2-[(2-methoxycarbonyl)ethylthio]-α-isopropenyl-4-oxo-3-(3'-bromophenoxyacetamido)-1-azetidineacetate;
t-butyl 2-[(2-ethoxycarbonyl)ethylthio]-α-isopropenyl-4-oxo-3-(4'-chloroacetoxyphenylacetamido)-1-azetidineacetate;
t-hexyl 2-[(2-sec-butoxycarbonyl)ethylthio]-α-isopropenyl-4-oxo-3-(3'-formyloxyphenoxyacetamido)-1-azetidineacetate;
p-nitrobenzyl 2-[(2-ethoxycarbonyl)ethylthio]-α-isopropenyl-4-oxo-3-(2'-nitrophenylacetamido)-1-azetidineacetate;
p-methoxybenzyl 2-[(2-methoxycarbonyl)ethylthio]-α-isopropenyl-4-oxo-3-(4'-nitrophenoxyacetamido)-1-azetidineacetate;
benzhydryl 2-[(2-methoxycarbonyl)ethylthio]-α-isopropenyl-4-oxo-3-(3'-cyanophenylacetamido)-1-azetidineacetate;
p-bromophenacyl 2-[(2-ethoxycarbonyl)ethylthio]-α-isopropenyl-4-oxo-3-(2'-cyanophenoxyacetamido)-1-azetidineacetate;
propionoxymethyl 2-[(2-n-propoxycarbonyl)ethylthio]-α-isopropenyl-4-oxo-3-(4'-trifluoromethylphenylacetamido)-1-azetidineacetate;
p-nitrobenzyl 2-[(2-ethoxycarbonyl)ethylthio]-α-isopropenyl-4-oxo-3-(3'-trifluoromethylphenoxyacetamido)-1-azetidineacetate;
t-butyl 2-[(2-ethoxycarbonyl)ethylthio]-α-isopropenyl-4-oxo-3-(2'-ethylphenylacetamido)-1-azetidineacetate;
acetoxymethyl 2-[(2-isopropoxycarbonyl)ethylthio]-α-isopropenyl-4-oxo-3-(4'-isopropylphenoxyacetamido)-1-azetidineacetate;
t-butyl 2-[(2-methoxycarbonyl)ethylthio]-α-isopropenyl-4-oxo-3-(3'-ethoxyphenylacetamido)-1-azetidineacetate;
p-nitrobenzyl 2-[(2-methoxycarbonyl)ethylthio]-α-isopropenyl-4-oxo-3-(4'-methoxyphenoxyacetamido)-1-azetidineacetate;
p-nitrobenzyl 2-[(2-n-butoxycarbonyl)ethylthio]-α-isopropenyl-4-oxo-3-(α-formyloxyphenylacetamido)-1-azetidineacetate;
p-methoxybenzyl 2-[(2-ethoxycarbonyl)ethylthio]-α-isopropenyl-4-oxo-3-(α-benzhydryloxyphenylacetamido)-1-azetidineacetate;
benzhydryl 2-[(2-isobutoxycarbonyl)ethylthio]-α-isopropenyl-4-oxo-3-(α-benzhydryloxycarbonylphenylacetamido)-1-azetidineacetate;
p-nitrobenzyl 2-[(2-methoxycarbonyl)ethylthio]-α-isopropenyl-4-oxo-3-(α-benzyloxycarbonylaminophenylacetamido)-1-azetidineacetate;
t-butyl 2-[(2-ethoxycarbonyl)ethylthio]-α-isopropenyl-4-oxo-3-(α-t-butyloxycarbonylaminophenylacetamido)-1-azetidineacetate;
p-nitrobenzyl 2-[(2-ethoxycarbonyl)ethylthio]-α-isopropenyl-4-oxo-3-(2'-thienylacetamido)-1-azetidineacetate;
2-[(2-methoxycarbonyl)ethylthio]-α-isopropenyl-4-oxo-3-phthalimido-1-azetidineacetic acid;
2-[(2-methoxycarbonyl)ethylthio]-α-isopropenyl-4-oxo-3-formamido-1-azetidineacetic acid;
2-[(2-ethoxycarbonyl)ethylthio]-α-isopropenyl-4-oxo-3-acetamido-1-azetidineacetic acid;
2-[(2-n-propoxycarbonyl)ethylthio]-α-isopropenyl-4-oxo-3-butyramido-1-azetidineacetic acid;
2-[(2-methoxycarbonyl)ethylthio]-α-isopropenyl-4-oxo-3-chloroacetamido-1-azetidineacetic acid;
2-[(2-isopropoxycarbonyl)ethylthio]-α-isopropenyl4-oxo-3-(4'-chloroacetamido-4'-benzhydryloxycarbonylvaleramido)-1-azetidineacetic acid;
2-[(2-methoxycarbonyl)ethylthio]-α-isopropenyl4-oxo-3-(4'-nitrobenzyloxycarbamido)-1-azetidineacetic acid;
2-[(2-t-butoxycarbonyl)ethylthio]-α-isopropenyl4-oxo-3-benzyloxycarbamido-1-azetidineacetic acid;
2-[(2-ethoxycarbonyl)ethylthio]-α-isopropenyl4-oxo-3-t-butyloxycarbamido-1-azetidineacetic acid;
2-[(2-ethoxycarbonyl)ethylthio]-α-isopropenyl-4-oxo-3-(2',2',2'-trichloroethoxycarbamido)-1-azetidineacetic acid;
2-[(2-t-butoxycarbonyl)ethylthio]-α-isopropenyl4-oxo-3-(4'-methoxybenzyloxycarbamido)-1-azetidineacetic acid;
2-[(2-isobutoxycarbonyl)ethylthio]-α-isopropenyl4-oxo-3-phenylacetamido-1-azetidineacetic acid;
2-[(2-ethoxycarbonyl)ethylthio]-α-isopropenyl4-oxo-3-phenoxyacetamido-1-azetidineacetic acid;
2-[(2-ethoxycarbonyl)ethylthio]-α-isopropenyl-4-oxo-3-(2',5'-dichlorophenylacetamido)-1-azetidineacetic acid;
2-[(2-isopropoxycarbonyl)ethylthio]-α-isopropenyl-4-oxo-3-(3'-bromophenoxyacetamido)-1-azetidineacetic acid;
2-[(2-ethoxycarbonyl)ethylthio]-α-isopropenyl4-oxo-3-(4'-chloroacetoxyphenylacetamido)-1-azetidineacetic acid;

2-[(2-methoxycarbonyl)ethylthio])-α-isopropenyl4-oxo-3-(3'-formyloxyphenoxyacetamido)-1-azetidineacetic acid;
2-[(2-ethoxycarbonyl)ethylthio]-α-isopropenyl-4-oxo-3-(2'-nitrophenylacetamido)-1-azetidineacetic acid;
2-[(2-n-propoxycarbonyl)ethylthio]-α-isopropenyl4-oxo-3-(4'-nitrophenoxyacetamido)-1-acetidineacetic acid;
2-[(2-methoxycarbonyl)ethylthio]-α-isopropenyl-4-oxo-3-(3'-cyanophenylacetamido)-1-azetidineacetic acid;
2-[(2-ethoxycarbonyl)ethylthio]-α-isopropenyl4-oxo-3-(2'-cyanophenoxyacetamido)-1-azetidineacetic acid;
2-[(2-n-butoxycarbonyl)ethylthio]-α-isopropenyl4-oxo-3-(4'-trifluoromethylphenylacetamido)-1-azetidineacetic acid;
2-[(2-ethoxycarbonyl)ethylthio]-α-isopropenyl-4-oxo-3-(3'-trifluoromethylphenoxyacetamido)-1-azetidineacetic acid;
2-[(2-ethoxycarbonyl)ethylthio]-α-isopropenyl-4-oxo-3-(2'-ethylphenylacetamido)-1-azetidineacetic acid;
2-[(2-isopropoxycarbonyl)ethylthio]-α-isopropenyl4-oxo-3-(4'-isopropylphenoxyacetamido)-1-azetidineacetic acid;
2-[(2-methoxycarbonyl)ethylthio]-α-isopropenyl-4-oxo-3-(3'-ethoxyphenylacetamido)-1-azetidineacetic acid;
2-[(2-methoxycarbonyl)ethylthio]-α-isopropenyl4-oxo-3-(4'-methoxyphenoxyacetamido)-1-azetidineacetic acid;
2-[(2-methoxycarbonyl)ethylthio]-α-isopropenyl4-oxo-3-(α-formyloxyphenylacetamido)-1-azetidineacetic acid;
2-[(2-ethoxycarbonyl)ethylthio]-α-isopropenyl4-oxo-3-(α-benzhydryloxyphenylacetamido)-1-azetidineacetic acid;
2-[(2-isobutoxycarbonyl)ethylthio]-α-isopropenyl4-oxo-3-(α-benzhydryloxycarbonyl-phenylacetamido)-1-azetidineacetic acid;
2-[(2-methoxycarbonyl)ethylthio]-α-isopropenyl4-oxo-3-(α-benzyloxycarbonylamino-phenylacetamido)-1-azetidineacetic acid;
2-[(2-ethoxycarbonyl)ethylthio]-α-isopropenyl-4-oxo-3-(α-t-butyloxycarbonylamino-phenylacetamido)-1-azetidineacetic acid;
2-[(2-ethoxycarbonyl)ethylthio]-α-isopropenyl-4-oxo-3-(2'-thienylacetamido)-1-azetidineacetic acid; and the like.

The following examples are provided to illustrate the preparation and utility of the compounds of this invention. They are not intended to be limiting upon the broad scope of the invention.

EXAMPLE 1

Preparation of 2-[(2-methoxycarbonyl)ethyl-sulfinyl]-α-isopropenyl-4-oxo-3-phthalimido1-azetidineacetic acid, methyl ester To 100 ml. of methyl acrylate were added 5 g. of methyl 6-phthalimido-2,2-dimethylpenam-1-oxo-3-carboxylate. The solution was refluxed for 16 hours under a nitrogen atmosphere. The solvent then was removed in vacuo to leave a residual white foam. The foam was dissolved in methanol, the solution was cooled, and the resulting crystals were removed (250 mg.) by filtration.

The filtrate was concentrated in vacuo to give a white foam comprising the title compound.

nmr (CDCl$_3$): 2.1 (3H, broad s), 2.8 (4H, m), 3.4 (3H, s), 3.5 (3H, s), 3.55 (3H, s), 3.6 (3H, s), 5.0–5.3 (3H, m), 5.4 (1H, d, J = 4 cps), 5.75 (1H, d, J = 4 cps), 5.9 (1H, d, J = 4 cps), and 7.9 Hz. (4H, broad m). ir (Nujol): 1795, 1785, and 1735 cm$^{-1}$.

EXAMPLE 2

Preparation of 2-[(2-methoxycarbonyl)ethylsulfinyl]-α-isopropenyl-4-oxo-3-phthalimido1-azetidineacetic acid, p-nitrobenzyl ester To 50 ml. of methyl acrylate were added 500 mg. of p-nitrobenzyl 6-phthalimido-2,2-dimethylpenam-1-oxo-3-carboxylate. The solution was refluxed for 18 hours under a nitrogen atmosphere. Solvent then was removed in vacuo to leave a residual white foam. The mixture was crystallized from methanol to give 60 mg. of white crystals of starting material. The filtrate, upon evaporation of the methanol, gave the acrylate adduct product as a white foam.

nmr (CDCl$_3$): 2.05 (3H, broad s), 2.83 (4H, broad s), 3.4 (3H, s), 3.65 (3H, s), 3.85 (3H, s), 5.0–5.5 (6H, broad m), 5.8 (2d, 1H each, J = 4 cps), 7.6 (2H, d), 7.8 (4H, s), and 8.2 Hz. (2H, d).

EXAMPLE 3

Preparation of methyl 7-phthalimido-3-methyl3-cephem-4-carboxylate

To a mixture of 10 ml. of N,N-dimethylacetamide, 20 ml. of benzene, and 0.06 ml. of methanesulfonic acid were added 650 mg. of 2-[(2-methoxycarbonyl)ethylsulfinyl]α-isopropenyl-4-oxo-3-phthalimido-1-azetidineacetic acid, methyl ester. The resulting solution was refluxed for 1.5 hours on a steam bath, and the solvent then was removed in vacuo. The resulting residue was purified by preparative thin-layer chromatography using a 3:7 mixture of ethyl acetate and benzene as eluant. A fraction of 156 mg. was recovered and identified as the title compound by comparison with an authentic specimen thereof.

EXAMPLE 4

Preparation of 2-[(2-methoxycarbonyl)ethylsulfinyl]-α-isopropenyl-4-oxo-3-phenoxyacetamido-1-azetidineacetic acid, p-nitrobenzyl ester To 150 ml. of methyl acrylate were added 5 g. of p-nitrobenzyl 6-phenoxyacetamido-2,2-dimethylpenam-1-oxo3-carboxylate. The resulting solution was refluxed for 3 days. The solvent then was removed in vacuo, and the resultant foam was dissolved in hot methanol. The methanol was cooled, and crystals of starting material (500 mg.) formed and were collected. An nmr spectrum of the filtrate indicated the presence of the title compound along with a small amount of starting material. An aliquot of the filtrate was purified by preparative thin-layer chromatography using a 3:7 mixture of ethyl acetate and benzene as eluant to obtain the title compound as a white foam.

nmr (CD$_3$Cl): 2.0 (3H, s), 2.8 (4H, m), 3.75 (3H, s), 4.62 (2H, s), 5.2 (4H, m), 5.4 (2H, s), 5.82 (1H, q, J = 4 cps and 10 cps), 7.0–7.6 (5H, m), 7.6 (2H, d, J = 8 cps), and 8.3 Hz. (2H, d, J = 8 cps).

EXAMPLE 5

Preparation of 2-[(2-ethoxycarbonyl)ethylsulfinyl]-α-isopropenyl-4-oxo-3-phenoxyacetamido-1-azetidineacetic acid, p-nitrobenzyl ester To 50 ml. of ethyl acrylate were added 5 g. of p-nitrobenzyl 6-phenoxyacetamido-2,2-dimethylpenam-1-oxo3-carboxylate. The mixture was refluxed for 24 hours. The solvent then was removed in vacuo. An nmr analysis of the residue indicated the presence of both starting material and the title compound. The residue was crystallized from methanol to recover 840 mg. of the starting material. The filtrate from the crystallization was chromatographed on silica gel using a 7:3 mixture of benzene and ethyl acetate as eluant to give 674 mg. of the title compound.

nmr ($CD_3Cl$): 1.18 (3H, t, J = 8 cps), 2.0 (3H, s), 2.8 (4H, m), 4.1 (2H, q, J = 8 cps), 4.6 (2H, s), 5.05 (1H, s), 5.1 (3H, broad s), 5.38 (2H, 2s), 6.2 (1H, q, J = 4 cps and 11 cps), 6.8–7.5 (5H, m), 7.6 (2H, d, J = 10 cps), and 8.23 Hz. (2H, d, J = 10 cps).

EXAMPLE 6

Preparation of 2-[(2-methoxycarbonyl)ethylsulfinyl]-α-isopropylidene-4-oxo-3-phthalimido-1-azetidineacetic acid, methyl ester The product from Example 1 (4.8 g.) was dissolved in 100 ml. of benzene, and 1 ml. of triethylamine was added. The mixture was maintained for one minute, and the solvent then was removed in vacuo to leave 4.8 g. of the title compound as a white foam.

nmr ($CDCl_3$): 2.4 (3H, s), 2.8 (4H, m), 3.35 (3H, s), 3.4 (3H, s), 3.65 (3H, s), 3.8 (3H, s), 3.82 (3H, s), 5.2 (1H, 2d, J = 4 cps each), 5.75 (1H, d, J = 4 cps), 5.95 (1H, d, J = 4 cps), and 7.8 Hz. (4H, m).

EXAMPLE 7

Preparation of 2-[(2-methoxycarbonyl)ethylsulfinyl]-α-isopropylidene-4-oxo-3-phthalimido-1-azetidineacetic acid, p-nitrobenzyl ester The product from Example 2 was dissolved in benzene, and 1 ml. of triethylamine was added. The mixture was maintained for one minute, and the solvent then was removed in vacuo to obtain the title compound.

EXAMPLE 8

Preparation of 2-[(2-methoxycarbonyl)ethylthio]-α-isopropenyl-4-oxo-3-phthalimido-1-azetidineacetic acid, methyl ester The product from Example 1 (500 mg.) was dissolved in a mixture of 50 ml. of carbon tetrachloride and 10 ml. of benzene, the latter containing 1 equivalent of phosphorous tribromide based upon 500 mg. of the product from Example 1. The solution was refluxed for 1.5 hours and then was washed with sodium bicarbonate solution and dried. The solvent then was removed in vacuo. The resulting residue was purified by preparative thin-layer chromatography on silica gel using a 3:7 mixture of ethyl acetate and benzene as eluant. The title compound (204 mg.) was obtained as a white foam.

nmr ($CD_3Cl$): 2.05 (3H, broad s), 2.7 (4H, m), 3.63 (3H, s), 3.9 (3H, s), 5.2 (3H, m), 5.75 (2H, s), and 7.8 Hz. (4H, s).

EXAMPLE 9

Preparation of 2-[(2-methoxycarbonyl)ethylthio]-α-isopropylidene-4-oxo-3-phthalimido1-azetidineacetic acid, p-nitrobenzyl ester To a mixture of 25 ml. of benzene and 280 mg. (1 eq.) of phosphorous tribromide were added 589 mg. of the product from Example 7. The resulting solution was stirred at room temperature with periodic monitoring of the content of the reaction mixture by thin-layer chromatography. Stirring was continued until chromatographic analysis showed the absence of starting material. Total stirring time was 45 minutes. The solution then was washed with sodium bicarbonate solution, dried over magnesium sulfate, and the solvent was removed in vacuo to obtain 532 mg. of the title compound as a yellow foam.

nmr ($CD_3Cl$): 2.28 (3H, s), 2.32 (3H, s), 2.47 (4H, m), 3.54 (3H, s), 5.37 (2H, s), 5.4 (1H, d, J = 4 cps), 5.63 (1H, d, J = 4 cps), 7.6 (2H, d, J = 10 cps), 7.8 (4H, s), and 8.3 Hz (2H, d, J = 10 cps).

EXAMPLE 10

Preparation of 2-[(2-methoxycarbonyl)ethylthio]-α-isopropylidene-4-oxo-3-phthalimido1-azetidineacetic acid The product from Example 9 (100 mg.) was dissolved in 25 ml. of tetrahydrofuran containing 0.5 ml. of 90 percent aqueous acetic acid. The solution was maintained at room temperature, and 1 g. of zinc dust was added. The mixture was stirred for one hour at room temperature after which it was filtered. The solid which was collected then was washed with ethyl acetate, and the ethyl acetate washed was added to the filtrate. The filtrate was concentrated in vacuo, and the residue was dissolved in a mixture of ethyl acetate and sodium bicarbonate solution. The sodium bicarbonate solution was separated from the ethyl acetate and was acidified to pH 2 by addition of 1N hydrochloric acid. The acidified aqueous mixture then was extracted with ethyl acetate. The ethyl acetate was evaporated in vacuo to obtain 35 mg. of the title compound as a white solid.

nmr ($CDCl_3$): 2.32 (3H, s), 2.38 (3H, s), 2.53 (4H, m), 3.54 (3H, s), 5.50 (1H, d, J = 4 cps), 5.72 (1H, d, J = 4 cps), and 7.87 Hz (m, J = 4 cps).

The above product exhibited antimicrobial activity. Using the disc plate assay, a concentration of 10 mg./ml. gave zone sizes in millimeters as follows:

*Staphylococcus aureus* — 14 mm.
*Bacillus subtilis* — 11 mm.
*Sarcina lutea* — 11 mm.

I claim:
1. A compound of the formula

$$R\underset{O}{\overset{}{\diagdown}}\!\!\!\diagup\!\!\!\underset{}{\overset{S-CH_2-CH_2-C-OR_a}{\diagdown}}$$

(structure: β-lactam ring with R substituent, S-$CH_2$-$CH_2$-C(=O)-O$R_a$ side chain, and =C($CH_3$)-COO$R_1$ group)

in which $R_a$ is $C_1$–$C_4$ alkyl;
$R_1$ is hydrogen or a carboxy protecting group; and
R is
(a) phthalimido;

(b) an amido group of the formula

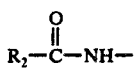

in which $R_2$ is (1) hydrogen, $C_1$-$C_3$ alkyl, halomethyl, thienyl2-methyl, 4-protected-amino-4-protected carboxybutyl, benzyloxy, 4-nitrobenzyloxy, t-butyloxy, 2,2,2-trichloroethoxy, 4-methoxybenzyloxy;

(2) a group of the formula $R'$-$(O)_m$-$CH_2$— in which m is 0 or 1, and $R'$ is phenyl or phenyl substituted with 1 or 2 halogens, protected hydroxy, nitro, cyano, trifluoromethyl, $C_3$-$C_4$ alkyl, or $C_1$-$C_2$ alkoxy;

(3) a group of the formula $$R'-CH- \atop W$$

in which $R'$ is as defined above and W is protected hydroxy, protected carboxy, or protected amino; or (c) an imidazolidinyl group of the formula

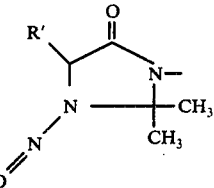

in which $R'$ is as defined above.

2. Compound of claim 1, in which $R_1$ is a carboxy protecting group.

3. Compound of claim 1, in which $R_a$ is methyl or ethyl.

4. Compound of claim 3, in which R is phenylacetamido or phenoxyacetamido.

* * * * *

UNITED STATES PATENT AND TRADEMARK OFFICE
CERTIFICATE OF CORRECTION

PATENT NO. : 4,115,383
DATED : September 19, 1978
INVENTOR(S) : Robin D. G. Cooper It is certified that error appears in the above-identified patent and that said Letters Patent are hereby corrected as shown below:

Column 23, line 22, "$C_3-C_4$" should read --$C_1-C_4$--.

Signed and Sealed this

Fourth Day of December 1979

[SEAL]

Attest:

SIDNEY A. DIAMOND

Attesting Officer

Commissioner of Patents and Trademarks